(12) United States Patent
Azernikov et al.

(10) Patent No.: US 10,157,330 B2
(45) Date of Patent: Dec. 18, 2018

(54) METHOD AND APPARATUS FOR SHAPE ANALYSIS, STORAGE AND RETRIEVAL OF 3D MODELS WITH APPLICATION TO AUTOMATIC DENTAL RESTORATION DESIGN

(71) Applicant: James R. Glidewell Dental Ceramics, Inc., Newport Beach, CA (US)

(72) Inventors: Sergei Azernikov, Irvine, CA (US); Sergey Vladimirovich Nikolskiy, Coto de Caza, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 1092 days.

(21) Appl. No.: 14/211,607

(22) Filed: Mar. 14, 2014

(65) Prior Publication Data
US 2014/0278279 A1    Sep. 18, 2014

Related U.S. Application Data

(60) Provisional application No. 61/799,110, filed on Mar. 15, 2013.

(51) Int. Cl.
*A61C 13/00* (2006.01)
*G06K 9/62* (2006.01)
*G06F 17/50* (2006.01)

(52) U.S. Cl.
CPC ........ *G06K 9/6215* (2013.01); *A61C 13/0004* (2013.01); *G06F 17/5009* (2013.01)

(58) Field of Classification Search
CPC ..... A61C 13/0004; A61C 5/77; A61C 9/0053; A61C 9/004; Y10T 29/49567; G06F 17/5009

USPC ................ 433/215, 201.1; 703/1; 700/98
See application file for complete search history.

(56) References Cited

U.S. PATENT DOCUMENTS

| | | | |
|---|---|---|---|
| 6,633,789 B1* | 10/2003 | Nikolskiy | G06F 19/321 433/2 |
| 7,428,481 B2* | 9/2008 | Nikolskiy | G06F 19/321 29/896.1 |
| 2004/0220691 A1* | 11/2004 | Hofmeister | A61C 13/0004 700/98 |

(Continued)

OTHER PUBLICATIONS

S. Wolthusen, et al., "Non-Forensic Odontological Biometrics," Fifth International Conference on Intelligent Information Hiding and Multimedia Signal Processing IIH-MSP'09, IEEE, Sep. 12, 2009, pp. 1105-1109.*

(Continued)

*Primary Examiner* — Kandasamy Thangavelu
(74) *Attorney, Agent, or Firm* — Dianne Burkhard

(57) ABSTRACT

A method for compact and descriptive representation of teeth shape, or other shapes, in terms of characteristic curves and its application to generation of automatic designs within dental CAD software or other software is provided. In an embodiment, a method includes capturing tooth shape by a network of characteristic curves, such as margin lines. In an embodiment, a method includes compactly encoding curves as strings, which then can be indexed and searched efficiently by similarity. In an embodiment, a method includes retrieving high quality crown design proposals from a case repository based on similarity of margin line.

20 Claims, 14 Drawing Sheets

(56) References Cited

U.S. PATENT DOCUMENTS

| | | | | |
|---|---|---|---|---|
| 2007/0026363 | A1* | 2/2007 | Lehmann | A61C 13/0004 433/223 |
| 2007/0203599 | A1* | 8/2007 | Shibata | A61C 13/0004 700/98 |
| 2007/0203600 | A1* | 8/2007 | Shibata | A61C 13/0004 700/98 |
| 2008/0261165 | A1* | 10/2008 | Steingart | A61C 13/0004 433/24 |
| 2009/0042167 | A1* | 2/2009 | Van Der Zel | A61C 1/084 433/215 |
| 2010/0281370 | A1* | 11/2010 | Rohaly | A61C 9/0053 715/719 |
| 2011/0213700 | A1 | 9/2011 | Sant'Anselmo | |
| 2012/0139142 | A1* | 6/2012 | Van Der Zel | A61C 13/0004 264/20 |
| 2012/0239177 | A1 | 9/2012 | Taub et al. | |
| 2013/0209965 | A1* | 8/2013 | Fisker | A61C 13/0004 433/220 |
| 2013/0218531 | A1* | 8/2013 | Deichmann | A61C 9/004 703/1 |
| 2013/0226534 | A1* | 8/2013 | Fisker | A61C 13/0004 703/1 |
| 2014/0032183 | A1* | 1/2014 | Fisker | A61C 13/0004 703/1 |
| 2014/0278278 | A1 | 9/2014 | Nikolskiey et al. | |

OTHER PUBLICATIONS

R. Vaddi, et al., "Contour Detection Using Freeman Chain Code and Approximation Methods for the Real Time Object Detection," Asian Journal of Computer Science and Information Technology, vol. 1, No. 1, 2011, pp. 15-17.*

International Search Report for PCT/US2014/28754 dated Aug. 20, 2014.

Kiattisin, S et al. "A match of x-ray teeth films using image processing based on special features of teeth", SICE Annual Conference, 2008. IEEE: Aug. 22, 2008; p. 97; col. 2, paragraph 2; a 98, columns 1-2.

Brisbiesca, E. "3D-curve representation by means of a binary chain code", Mathematical and computer modelling 40.3(2004):285-295; 2004; p. 292, paragraph 2; p. 293, paragraph 1.

Cui, M, Femiani, J., Hu, J., Wondka, Razada A. "Curve matching for open 2D curves", Pattern Recognition Letters 30 (2009): pp. 1-10.
Wolfson, H. "On Curve Matching", Robotics Research Technical Report Technical Report No. 256, Robotics Report 86; Nov. 1986.
Gumhold, Stepfan et al. "Feature Extraction From Point Clouds." Scientific Computing and Imaging Institute 2001, in 13 pages.

* cited by examiner

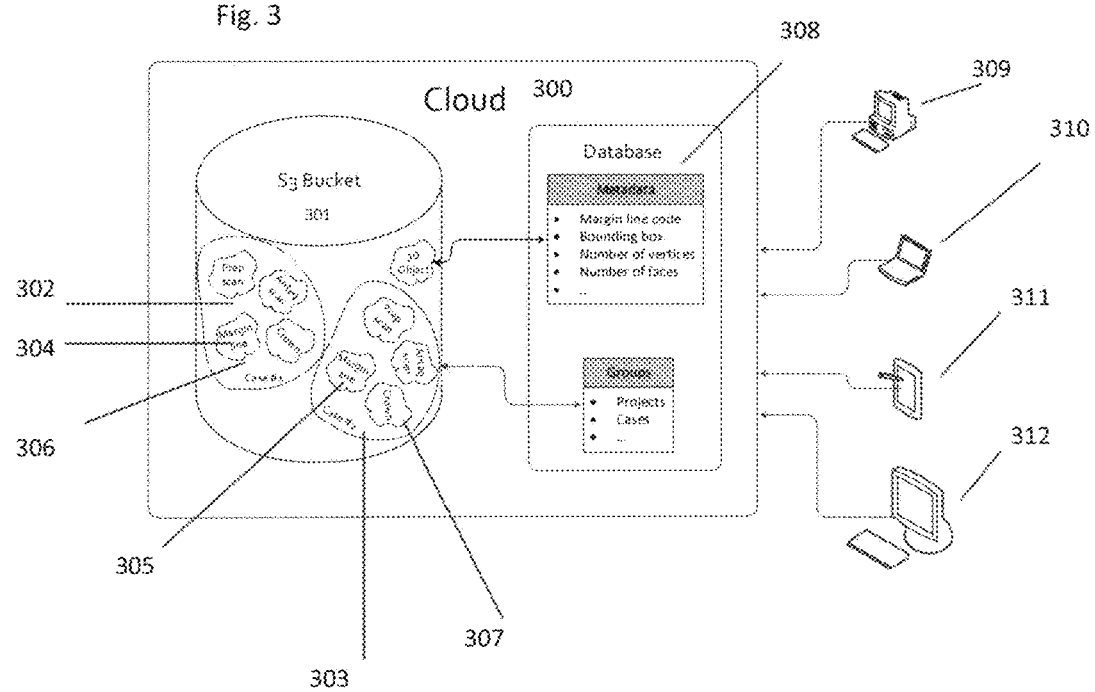

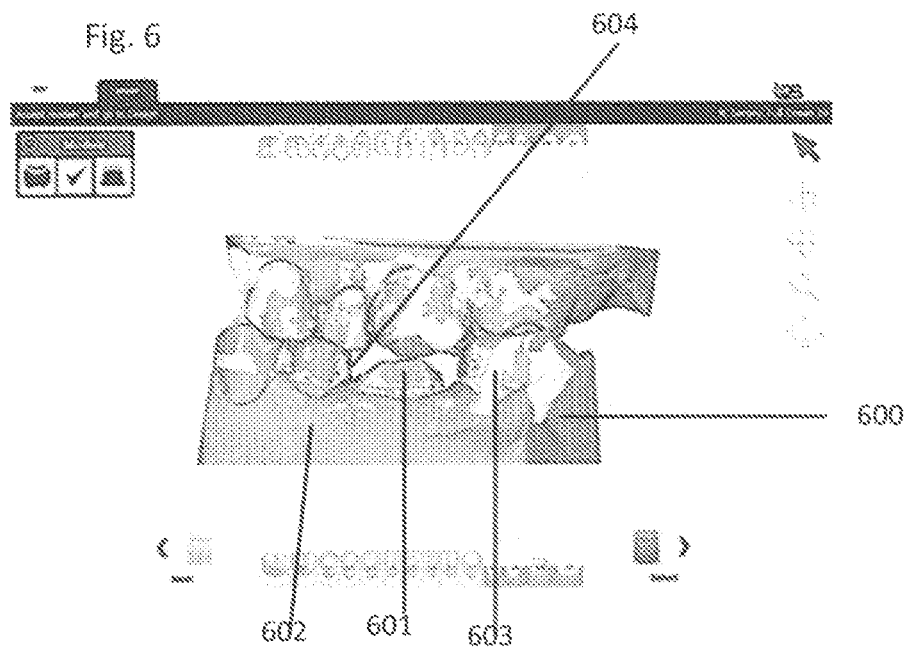
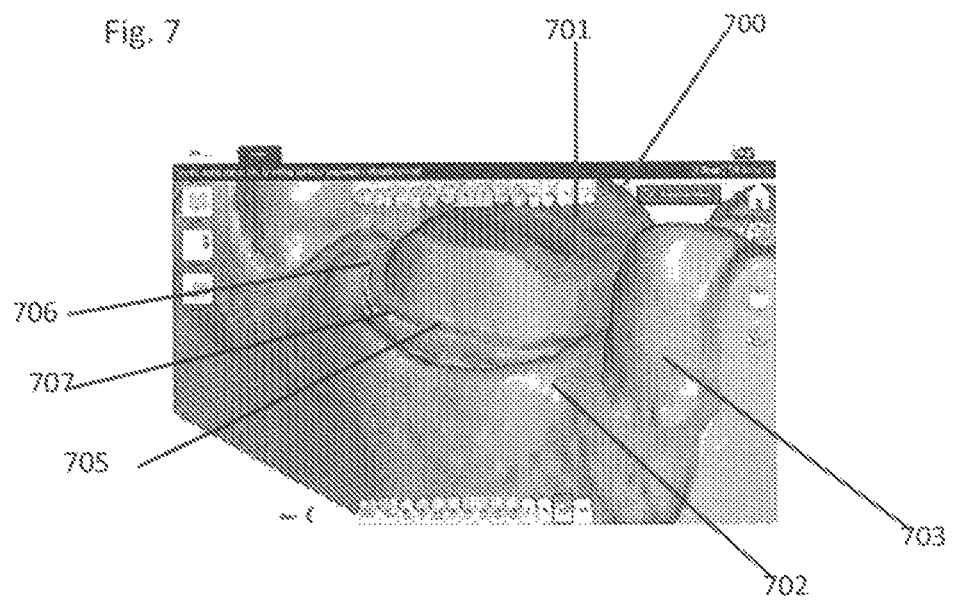

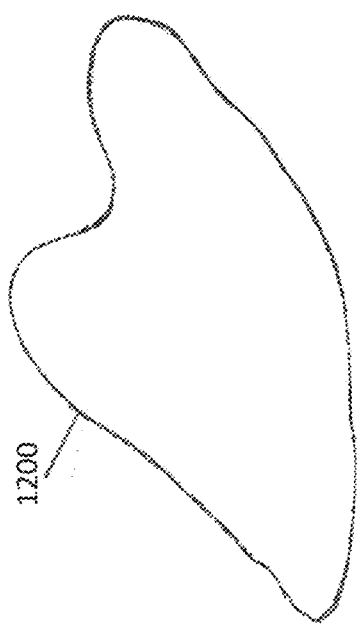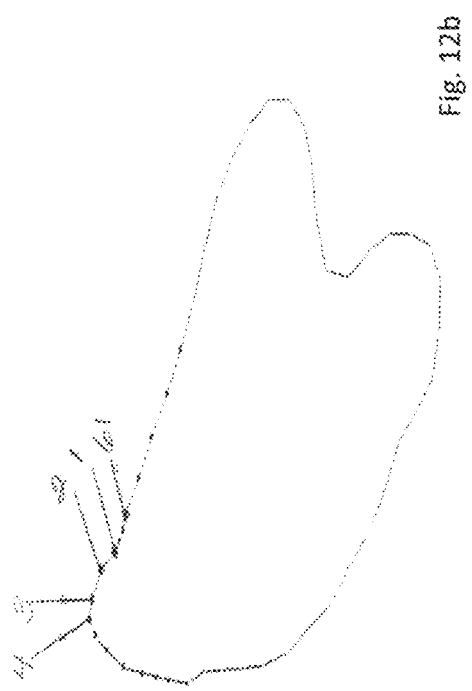

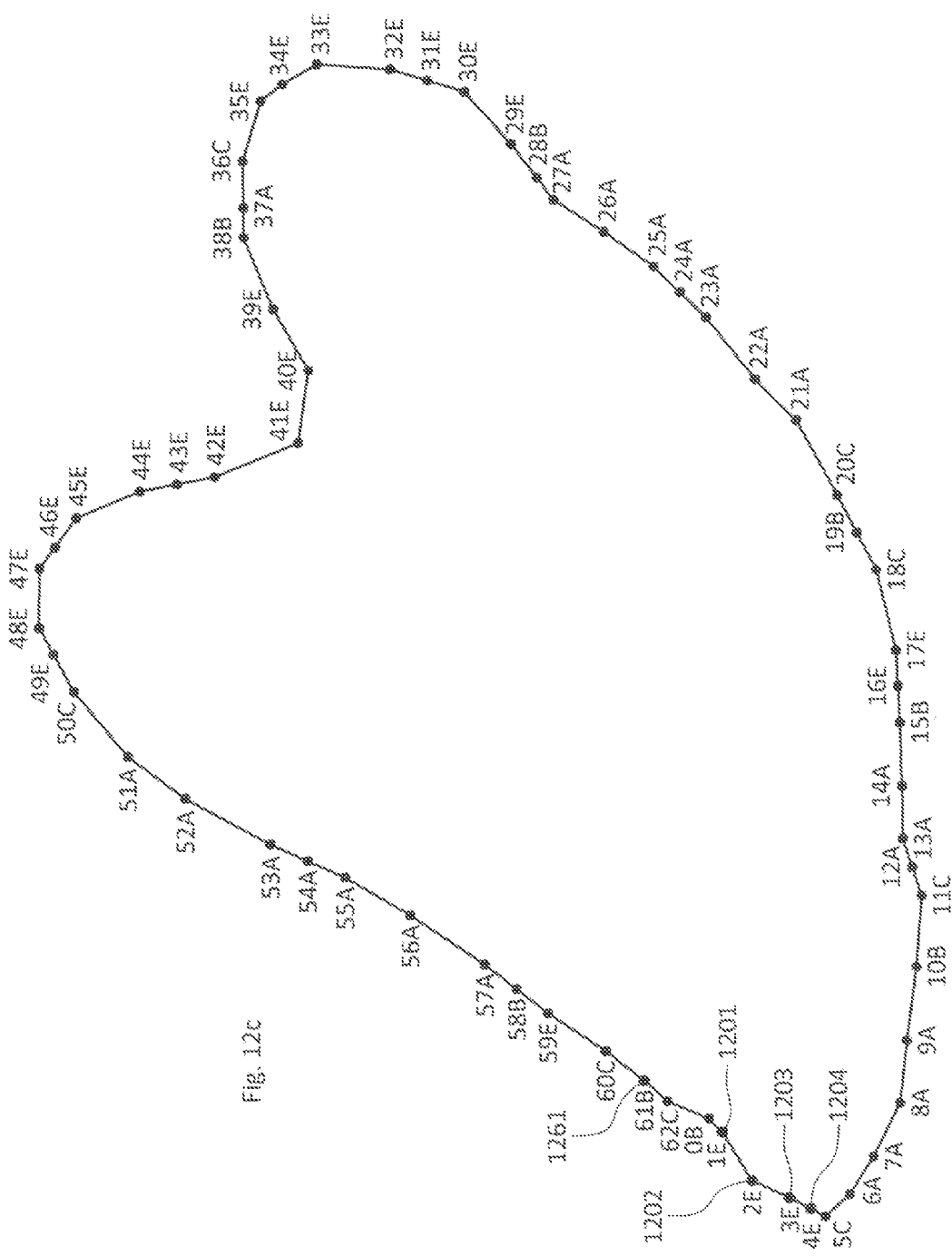

METHOD AND APPARATUS FOR SHAPE ANALYSIS, STORAGE AND RETRIEVAL OF 3D MODELS WITH APPLICATION TO AUTOMATIC DENTAL RESTORATION DESIGN

CROSS-REFERENCE TO RELATED APPLICATION

This application claims the benefit of U.S. Provisional Application Ser. No. 61/799,110 filed Mar. 15, 2013, the contents of which are hereby incorporated by reference herein.

FIELD

The present disclosure generally relates to methods for shape analysis, encoding of curves, storage and retrieval of 3D (three-dimensional models, and applications of such methods, including applications to dental CAD automation.

BACKGROUND

Computer-Aided Design (CAD) and Computer-Aided Manufacturing (CAM) are used in the field of dentistry to provide a range of products including crowns, veneers, inlays and onlays, fixed bridges, dental implant restorations, and orthodontic appliances. Typically, a dental CAD session starts from a generic library or templates to automatically generate a design proposal for a restoration. A library locally stored on a computer may frequently contain only a single generic representative tooth template for a given tooth number from which a restoration design is created. Due to the high anatomic variability, a large amount of deformation of the restoration design on the part of a design technician is required in order to produce the final tooth shape.

It would be desirable to have a method that automatically generates proposals which are much closer to the final shape of an acceptable dental restoration.

SUMMARY

A method is provided for compact and descriptive representation of shapes, such as teeth shape, by shape descriptors, such as characteristic curves, and the application of the method to the generation of automatic designs within dental CAD software or other software. In one embodiment, shapes can be captured by shape descriptors that are used to characterize aspects of the overall shape of an object and that are searched more efficiently than the shape directly. In an embodiment, a tooth shape can be faithfully captured by a network of characteristic curves, such as margin lines. Characteristic curves are shape descriptors that include features that are distinctive of certain shapes, and may be used to characterize aspects of the overall shape of the object, such as a shape of a tooth. The characteristic curves can be sampled and encoded in a manner that captures the localized curve behavior. In one embodiment, characteristic curves are compactly encoded as strings, which then can be indexed and searched efficiently by similarity.

In a further embodiment, high quality crown design proposals suitable for a restoration can be retrieved from a case repository of previously designed cases based on similarity of the case margin lines and the margin line of a preparation of the restoration tooth. It has been found that margin lines are characteristic curves that can provide information regarding the overall tooth shape. Thus, a design proposal for a tooth having an overall shape suitable for a patient's dentition can be generated by selecting a previously designed restoration from a case repository that has a margin line similar to the margin line of the preparation. By leveraging from a vast number of previously completed dental design restorations that have characteristic curves that have been encoded, and that can be searched and indexed, proposals for a tooth restoration may be generated that are much closer to an acceptable final shape than by traditional design methods. In some embodiments, cloud architecture is utilized to provide efficiency in storage, search, retrieval, and/or automatic proposal generation based on shape descriptors.

In one embodiment, a method for generating design proposals is provided that comprises the steps of capturing the shape of an object to be restored, by a shape identifier that characterizes the overall shape of the object. The method further comprises accessing a case repository of similar previously designed restoration cases, where each case comprises a digital 3D model of a shape, and data comprising a representation of a shape identifier of the shape. The shape descriptors can be indexed and searched efficiently by measuring the similarity between the shape identifier of the shape of the object to be restored and the shape descriptors of the previously designed restoration cases. Design proposals can be generated by retrieving digital 3D models of previously designed restorations from the case repository as design proposals, based on the measure of similarity.

In one embodiment, a method for generating dental design proposals comprises one or more of the following steps: (1) capturing tooth shape by identifying a network of characteristic curves; (2) compactly encoding curves as strings, which then can be indexed and searched efficiently by similarity; and (3) retrieving high quality design proposals, such as crowns, from a case repository based on similarity of characteristic curves. In one embodiment, methods may comprise generating restoration proposals by searching for similar cases in a database, and using the closest completed design as the proposal.

In one embodiment, a method for generating crown design proposals comprises capturing tooth shape by margin lines; encoding margin lines to obtain chain codes that can be indexed and searched efficiently by similarity; and retrieving high quality crown design proposals for a tooth restoration, from a case repository based on similarity of margin lines. In one embodiment, the method comprises searching for similar cases in a case repository, and using the closest completed crown as the design proposal.

It should be appreciated that such apparatus can be useful for many other applications including applications outside the dental domain, such as 3D search engines, real-time recognition and tracking of 3D objects and others.

BRIEF DESCRIPTION OF THE DRAWINGS

FIG. 3 depicts an embodiment of a system described herein.
FIG. 6 shows an image of a tooth preparation.

FIG. 7 shows an embodiment of a system for lining a margin of a tooth preparation.

FIGS. 12a, 12b, and 12c depict an embodiment of a curve encoding process.

While the above-identified drawings set forth presently disclosed embodiments, other embodiments are also contemplated, as noted in the detailed description. This disclosure presents illustrative embodiments by way of representation and not limitation. Numerous other modifications and embodiments can be devised by those skilled in the art which fall within the scope and spirit of the principles of the present disclosure.

DETAILED DESCRIPTION

Exemplary embodiments of methods and systems for shape analysis, encoding of curves, storage and retrieval of digital 3D (three-dimensional) models, and applications of such methods, including applications to dental CAD automation, are provided.

In one embodiment, a method for generating design proposals for a restoration comprises: (1) capturing a shape of an object to be restored, by a shape identifier; (2) accessing a case repository of similar previously designed restoration cases, where each case comprises a digital 3D model of a shape and a shape identifier that can be indexed and searched efficiently by similarity; and (3) retrieving digital 3D models of previously designed restorations from the case repository as design proposals, based on the similarity of the shape identifier of the object to be restored and the shape descriptors of the previously designed restorations. Characteristic curves, bounding boxes, boundary representations, and sets of points, are examples of shape descriptors that may be used to capture aspects of shape and provide a simplified representation of a shape.

Figure 1:
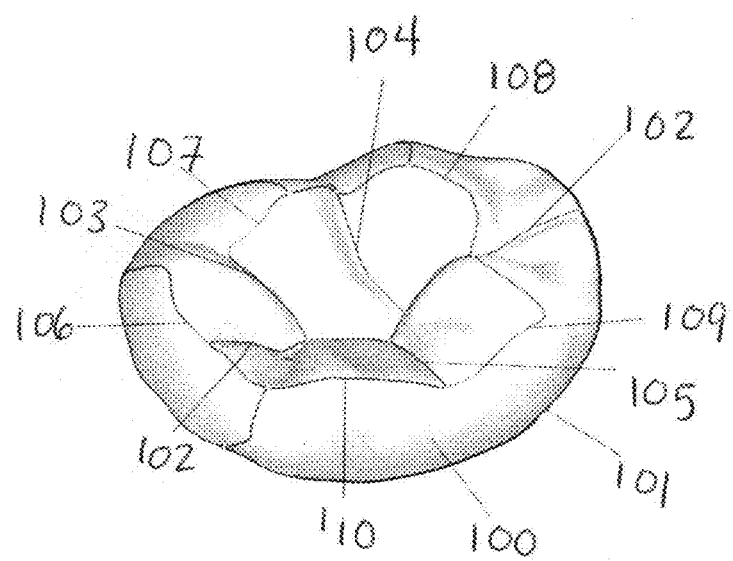
FIG. 1 is an illustration of a tooth.

In an embodiment, a method for compact and descriptive representation of teeth shape and generation of automatic designs within CAD may comprise one or more of the following steps: (1) capturing tooth shape by a network of characteristic curves; (2) compactly encoding the characteristic curves as strings; and (3) retrieving high quality design proposals from a case repository. FIG. 1 exemplifies characteristic curves of a tooth which individually, or as a network, may provide information regarding the overall shape of a tooth. In one embodiment, a margin line (101) is used as a characteristic curve to capture tooth shape, and margin lines can be encoded as a string by the methods described herein. Additional characteristic curves include grooves, such as central (102), distobuccal (103), mesiobuccal (104), and lingual (105) developmental grooves, and ridges including distal marginal (106), distobuccal cusp (107), mesiobuccal cusp (108), mesiolingual cusp (109), and distolingual cusp (110) ridges.

Figure 2:
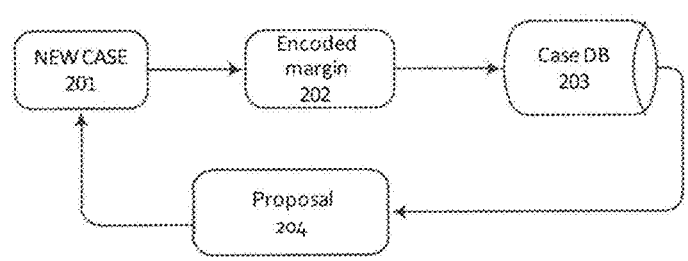
FIG. 2 depicts an embodiment of a method for automatic proposal generation.

FIG. 2 depicts an automatic proposal generation workflow (200) for one embodiment of a tooth restoration described herein. A new case of a tooth in need of restoration (201) is obtained. The workflow may comprise encoding a margin line of the tooth preparation (202); searching a case repository of previously designed dental restoration cases having encoded margin lines (203) for the same tooth number as the tooth preparation; and retrieving at least one design proposal from the case repository based on similarity measurements between the encoded margin lines from the previously designed restoration cases, and the encoded margin line of the tooth preparation (204).

In one embodiment, a case repository as exemplified in FIG. 3 (301) is obtained that comprises previously designed dental restoration cases (for example, 302 and 303). In one embodiment, the case repository comprises cases of previously designed restorations, such as crowns (e.g., 306, 307), having characteristic curves, such as margin lines, that have been encoded to form a chain code (i.e., margin line code). A database (308) may be associated with the case repository that comprises metadata comprising the chain codes for the previously designed restorations. One method for generating a design proposal for a dental restoration, such as a crown, comprises obtaining data for a tooth preparation that comprises a chain code for an encoded characteristic curve of the tooth preparation, such as the margin line; accessing a case repository of previously designed dental restoration cases, wherein each case comprises data comprising chain codes for encoded characteristic curves and a digital 3D model of a restoration; searching the case repository by measuring the similarity between the chain codes of encoded characteristic curves of previously designed dental restoration cases and the chain code of the encoded characteristic curves of the preparation; and retrieving a plurality of digital 3D models from the case repository as design proposals, based on similarity measurements of the characteristic curves of the tooth preparation and the previously designed dental restoration cases. In one embodiment, the characteristic curves may be compactly encoded as strings which may be searched by similarity measurements.

Shape descriptors, such as characteristic curves, may be used to represent the overall shape of a restoration such as a crown or bridge. Shape descriptors may be distinctive for identifying teeth by specific teeth numbers. It has been found that shape descriptors, such as characteristic curves, may provide information regarding the overall shape of a tooth that can be used in generating design proposals for individual restorations.

Figure 4A:
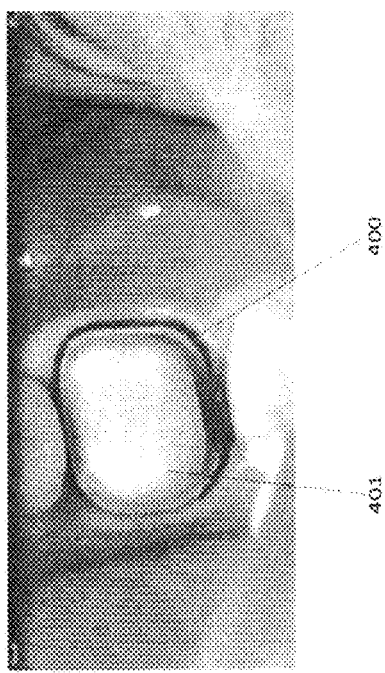
FIG. 4a depicts a scan of a tooth preparation.
Figure 4B:
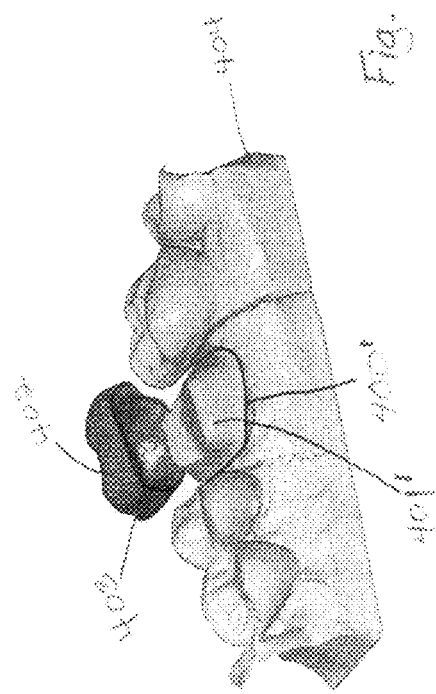
FIG. 4b shows an embodiment in which margin lines are marked on the tooth preparation and a restoration crown.

As exemplified by FIGS. 4a and 4b, a margin line (400, 400') is the area of contact between a preparation (401, 401') and a restoration, such as a crown (402), or other prosthesis. It has been found that in many instances, the margin line of a tooth provides a consistent characterization of the overall shape of a tooth. Therefore, restoration proposals generated by margin line comparisons may fit well within the patient's existing dentition. A high measure of similarity between the margin line of a tooth preparation and the margin lines of previously designed cases may generate design proposals having an overall tooth shape that is more suitable for use as a tooth restoration than proposals having a lower measure of margin line similarity.

Figure 5:
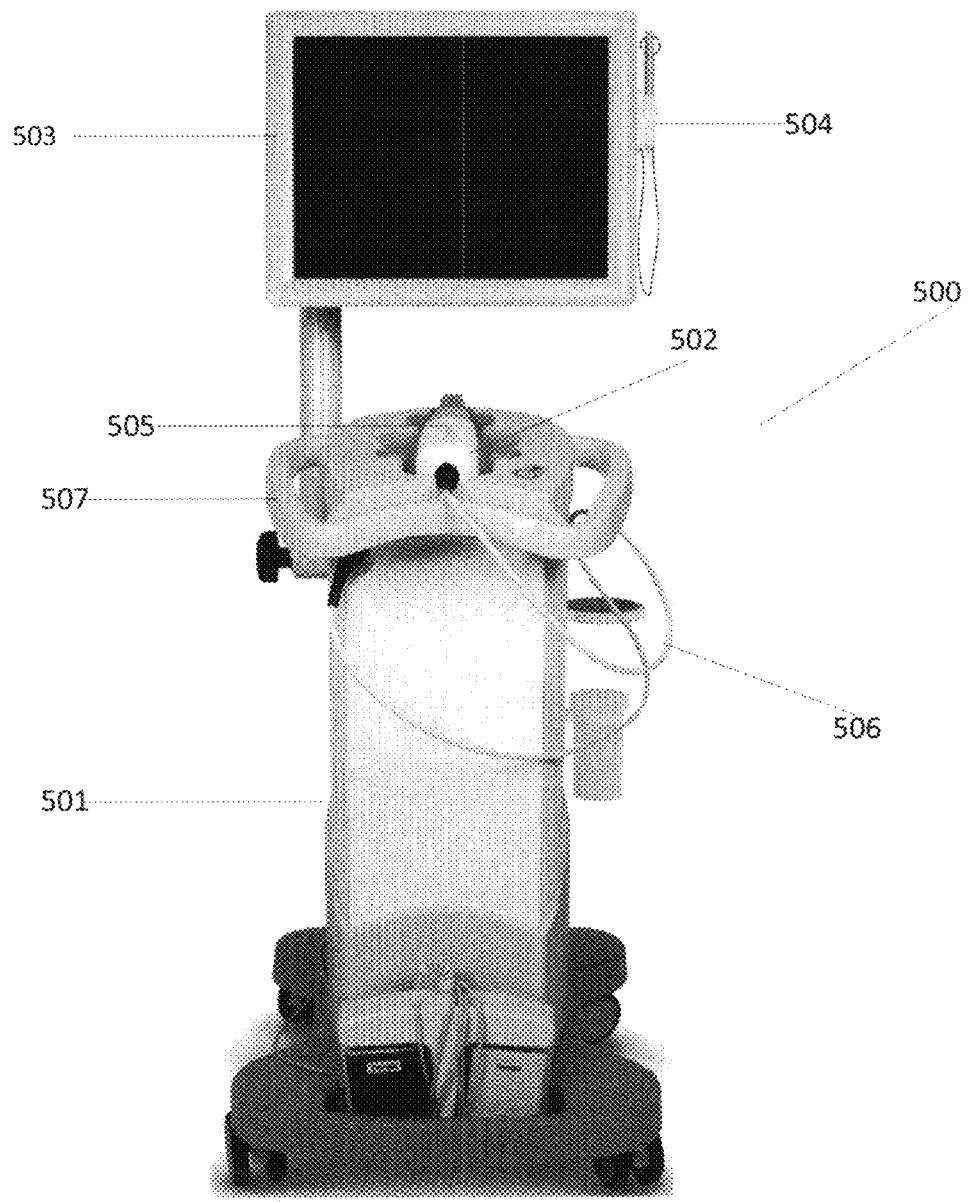
FIG. 5 shows an example of a scanning system.

A method for obtaining the margin line of a tooth, or a margin line of a preparation of a tooth to be restored, is provided. Clear margin lines may be useful for achieving good fit of the crown. A 3D model (404') of a preparation (401'), as seen in FIG. 4*b*, may be generated from images obtained by intra-oral scanning, or by scanning a physical impression from the patient's mouth. With reference to FIG. 5, a typical intra-oral scanning system (500) suitable for scanning a tooth preparation comprises a base unit (501) that serves as a housing for a microprocessor or computer, a scanning device (502), and a user interface, for example in the form of a touch screen (503). The scanning system (500) may also include a user input device (504), for example, a stylus that interfaces with the touch screen (503) to allow the user to interact with the scanning system (500). The scanning device (502) may include a wand (505) with a probe having a profile and size that provides sufficient clinical access to obtain suitable intra-oral images of a patient to identify a preparation. The wand may be connected to the computer by a cord (506), and the scanning system (500) may include a cradle (507) for holding the scanning device (502).

Intra-oral imaging technologies and products are currently available for use in scanning a patient's mouth to design a restoration. Examples include FastScan® (IOS Technologies, Inc.), CEREC® (Sirona), E4D (D4D Technologies), True Definition Scanner (3M ESPE), Trios® (3Shape), and iTero™ (Cadent/Align Technologies, Inc.). The intra-oral scanners may provide accurate acquisition and transfer of patient oral image information from the dental chair to the restoration designer. Alternatively, an impression of the preparation to be restored may be obtained by traditional impression making processes used in dental restoration, including forming an impression by the use of trays. The impression may be scanned directly, for example by a table-top or box scanner. Alternatively, the impression may be used to form a stone model which may then be scanned in the same manner.

A plurality of scans may be obtained in order to form a suitable image of the patient's oral anatomy. For example, occlusal, lingual and buccal scans may be taken of the preparation and the opposing jaw. In some embodiments, interproximal scans may be taken to capture the contact areas of neighboring teeth. A scanning system may be used to assemble the plurality of scans into a digital model (600) of the tooth preparation (601) and surrounding (602, 603) and opposing teeth (604), as shown, for example in FIG. 6. A model of a patient's oral anatomy providing margin line information may be stored locally, or remotely, for example, in an .stl format, for use in the methods described herein.

Figure 8:
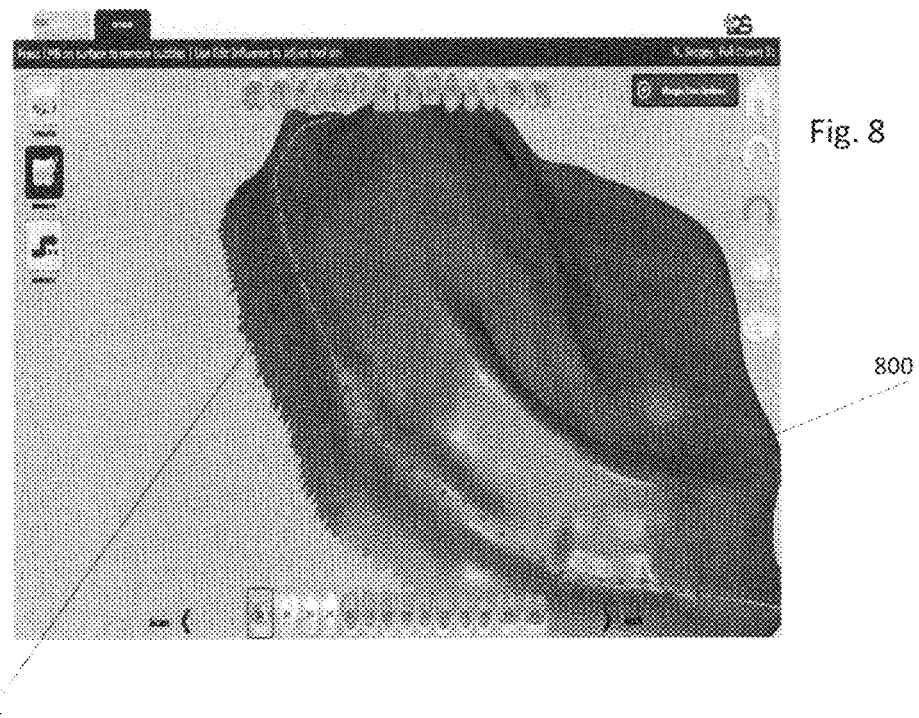
FIG. 8 shows an image of a tooth preparation and a margin line.
Figure 9:
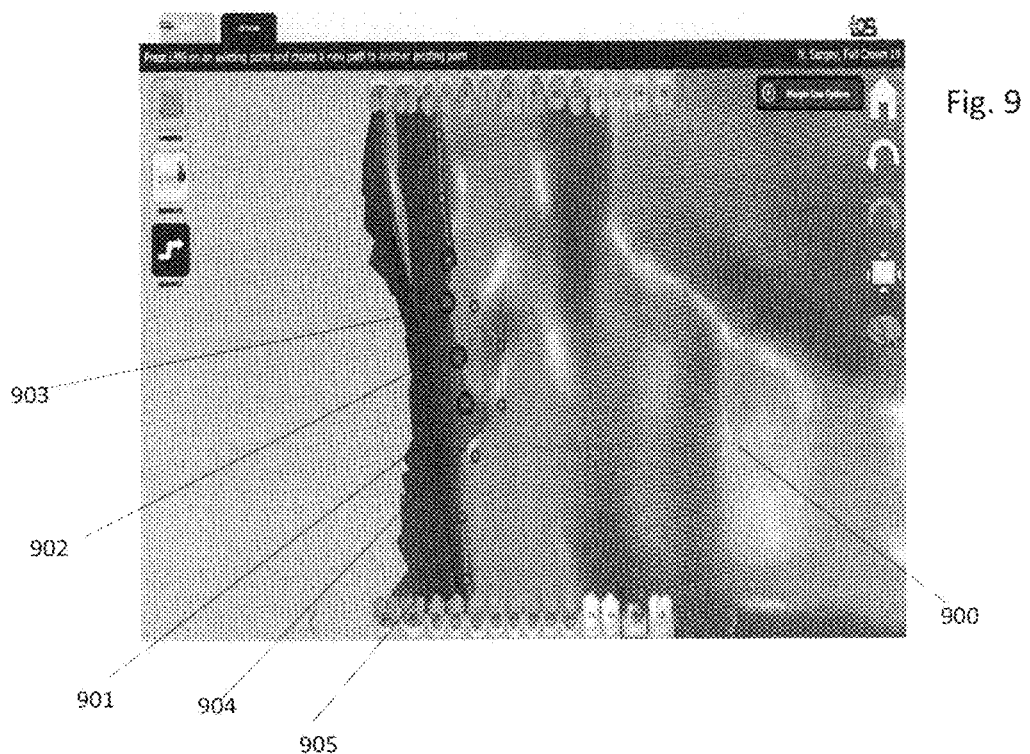
FIG. 9 shows an image of a tooth preparation and a margin line.

To identify and line a margin, a scanned model of a patient record is obtained and presented on a monitor as a 3D image as shown in FIG. 7 (700). The virtual representation of the tooth preparation (701) may depict the surrounding gingiva (702), neighboring teeth (703, 704), and optionally, opposing teeth (not shown). In one embodiment, a dental design program comprising executable program instructions may be used for lining a margin, as follows. The margin (705) of the tooth preparation is identified on the model and a starting point (707) for lining the margin of the preparation (701) is selected manually by a user interface, or automatically based on instructions provided by a computer program. A monitor of a computing system may be used to view the user interface of the program to select the starting point, or to modify features of the preparation prior to lining the margin. Where the margin is lined manually, a user may place a cursor of a design system over a point on the margin (705) by a user interface device, such as a mouse, placing a first point (707) on the margin (705). Computer executable instructions are provided to follow the contour of a margin (705) from the starting point to provide a margin line (706) around the remainder of the margin as exemplified in FIG. 8, to provide a margin line (801). Optionally, a user may adjust or relocate the margin line (801) on the image (800) with user interface devices. As exemplified in FIG. 9, one or more new points (901, 902, and 903) may be placed on the existing margin (904) to reroute the margin line (903) around the preparation (900). Artifacts that obscure a clear margin may also be removed manually by a user with user interface tools, or automatically detected and removed by computer executable instructions. Software programs for identifying margins, lining margins and/or removing artifacts, may be commercially available, and may include FastDesign™ Software (IOS Technologies) or 3Shape™ dental design software products.

The resulting margin lines may be encoded by a curve encoding process for use in the design proposal generation methods described herein.

Figure 10:
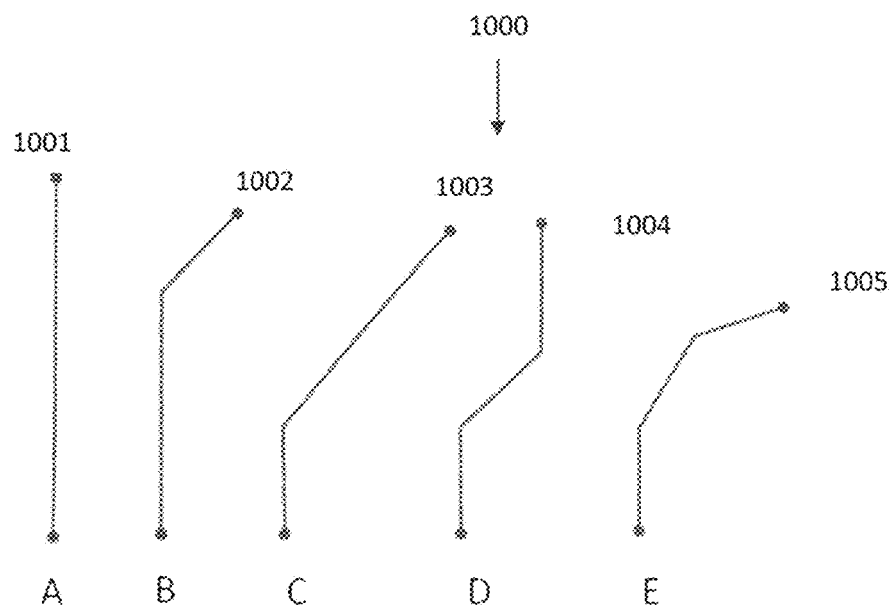
FIG. 10 shows a curve encoding alphabet used in an embodiment of the present disclosure.

Direct searching in large case repositories of general 3D curves is a computationally expensive task. One commonly used approach is adaptive sampling of the curve and working with resulting sparse polylines. However, dense sampling may be required to represent high curvatures and/or small features. Thus, methods for encoding characteristic curves, such as margin lines, and design proposal generation are described herein. In an embodiment of the present disclosure, a curve encoding process is described wherein curve shape is encoded using a pre-defined alphabet (1000), as shown in FIG. 10. Each letter in the alphabet represents certain local behavior (1001, 1002, 1003, 1004, and 1005) of the discretized curve.

Figure 11:
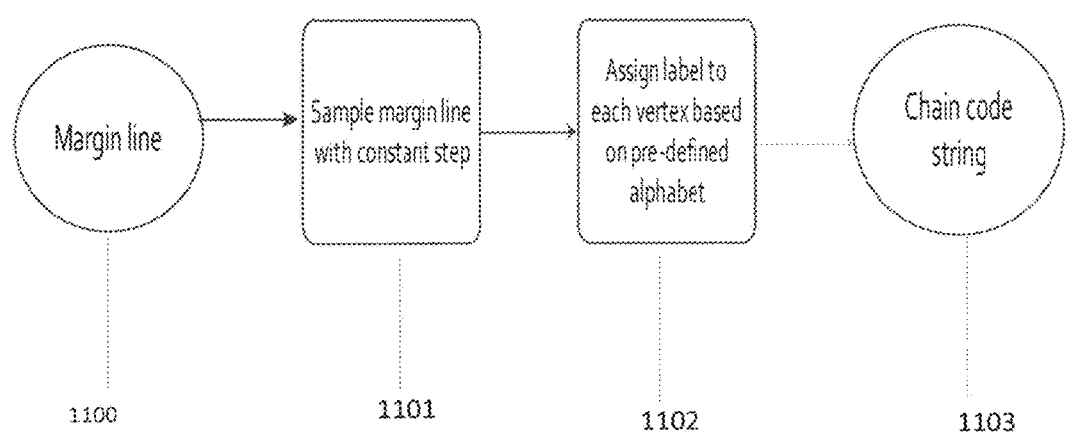
FIG. 11 shows a flow diagram of a method of forming a chain code.

FIG. 11 shows a flow diagram of one method for encoding a margin line of a restoration that comprises the steps of defining a margin line (1100), for example by lining the margin of a tooth preparation; sampling the margin line (1101) at a constant density; detecting localized behavior of a portion of the curve and assigning a label based on a pre-defined labeling system (1102); and linking the labels together to form a searchable chain code or string (1103).

In one embodiment depicted in FIGS. 12*a*, 12*b*, and 12*c*, the margin line (1200) is converted from a continuous line to a polyline with approximately equally distributed vertices (FIG. 12*b*). The given parametric curve may be sampled with constant density, for example, 0.5 mm, by computer executable instructions. In one embodiment, a starting point (for example, FIG. 12*b*, point 1) for sampling the margin line is selected on the buccal surface of a tooth or preparation. The starting point may be selected manually via a user interface tool by which a user places a starting point on the margin line; alternately, a starting point for sampling may be automatically identified or selected, via computer executable instructions providing directions as to the location of an appropriate starting point. In one embodiment, as exemplified in FIGS. 12*a*, 12*b*, and 12*c*, a method comprises sampling the margin line 1200 directionally, for example, by starting on point 1 on a buccal surface, and sampling the margin line in the buccal direction for the length of the margin line.

Figure 13:
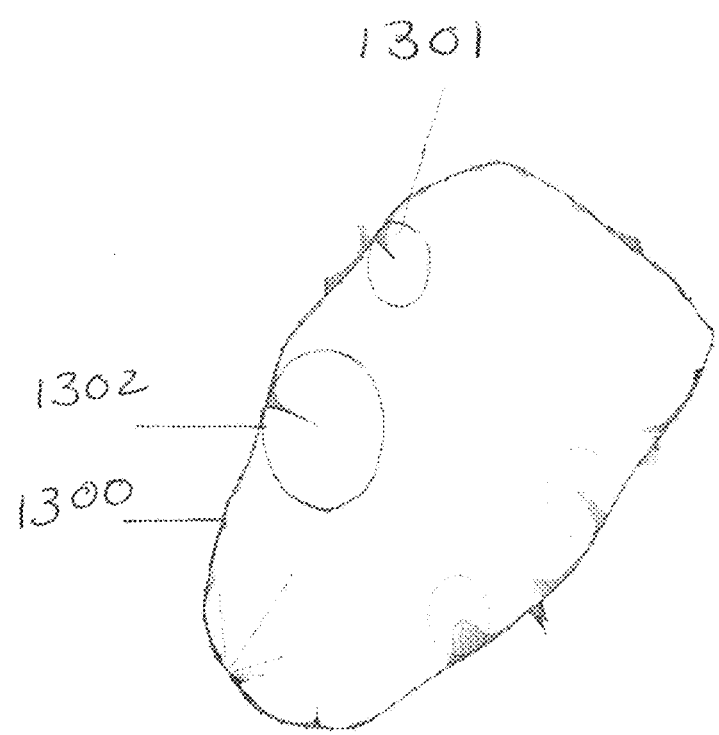
FIG. 13 depicts a radius of curvature of a margin line and osculating circles.

Constant density refers to a sample rate for identifying points on a curve that remains approximately the same throughout the curve sampling process. The curve may be sampled at any density that is suitable for detecting localized behavior that identifies distinct characterization of the overall shape of the object to be encoded. If the density or sample distance is too great or too small for a given curve, the specific curve behavior that characterizes or captures an overall shape may not be identified. FIG. 13 depicts one example of a margin line (1300) with osculating circles (1301, 1302, 1303) that indicate the local radius of curvature. In one embodiment, where a margin line has a minimum radius of curvature of about 0.5 mm, a sample density of about 0.5 mm may provide sufficient information about the behavior of the curve to identify the overall shape of the tooth.

The method for encoding a characteristic curve further comprises associating a label with a sample point based on localized behavior of the curve in the region of the sample point. In one embodiment, as exemplified in FIGS. 12b and 12c, the behavior over a set of three points (for example, points 1, 2, and 3) may be detected and a label, such as A, B, C, D, or, E, representing that behavior may be associated to point 1 (FIG. 12b, at 1201). The behavior of a further set of sampled points (for example, points 2, 3, and 4) is detected and a label that identifies this behavior is associated with a sample point. The method of detecting behavior and associating a label for that behavior may continue similarly for the remainder of the curve (for example to point 61, associating labels, e.g., 1202, 1203, 1204, and through to 1261). Encoding may be performed in a counter clockwise or clockwise direction around a curve. Alternately, a given curve may be encoded two times, in both the clockwise and counterclockwise directions.

Figure 14A:
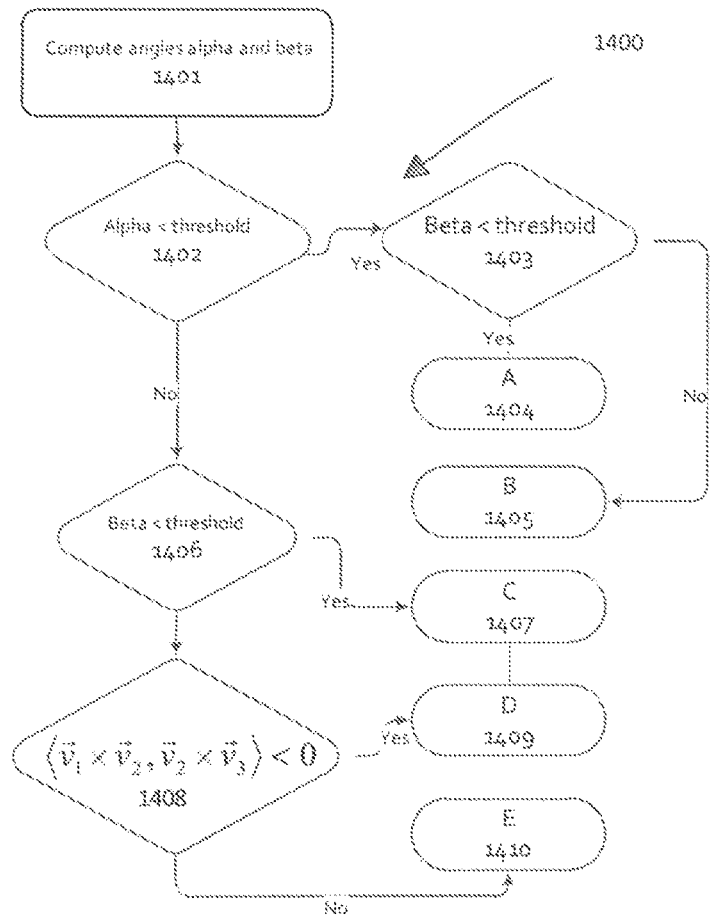
FIGS. 14a and 14b depict a process of encoding a characteristic curves according to one embodiment.
Figure 14B:
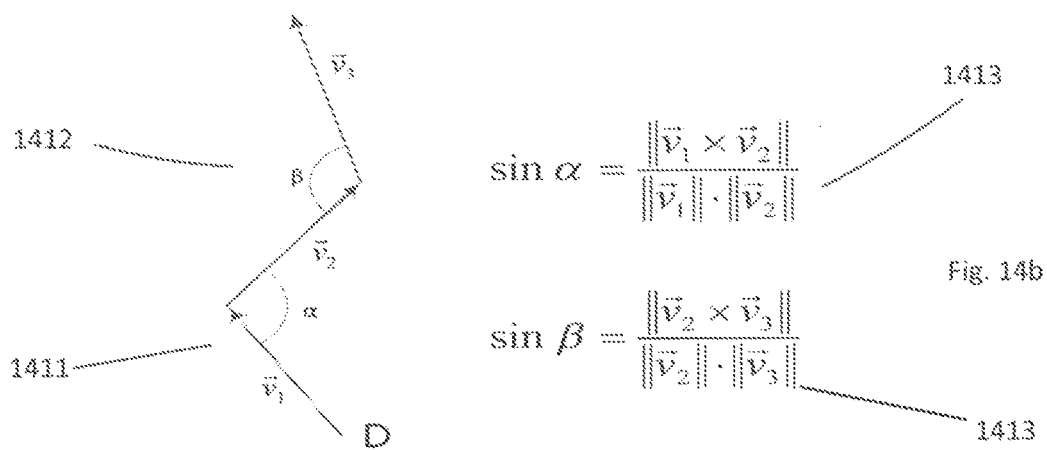

The flow diagram of FIG. 14a, and FIG. 14b, provide one example of a method for detecting the localized behavior of a curve and associating a label based on that behavior, as exemplified by the labels in FIG. 10. Computer-executable instructions may be provided by which angles of a curve are computed (1400) to determine the localized behavior (1401). In this example, the letter A (1404) is associated with a sample point where localized behavior of the curve is substantially smooth, and angles (alpha (1411) and beta (1412)) are below a defined threshold (1402, 1403). Likewise, B (1405) is associated with a sample point where the angle of a curve (alpha) is below a defined threshold (1402) for a portion of the sample region, and the angle beta (1403) is above a threshold, having a turn, in another portion of the curve. The letter C (1407) depicts localized behavior of curve having a first turn or angle (alpha) greater than a defined threshold, followed by no detectable angle or turn (1406). The letter D (1409) may be used to represent an area of the curve over a set of sample points wherein the localized behavior comprises a first detectable angle or turn in a first direction, and a second detectable angle or turn in second direction that is different from the first (1408); and the letter E (1410) may be used to represent localized behavior having a first detectable angle or turn in a first direction, and a second angle or turn in a similar direction. FIG. 14b depicts behavior calculations (1413) for angles alpha and beta. Linked together, these labels, as depicted in FIG. 10c constitute a chain code that may be represented as strings, stored in a searchable format, and linked to a file comprising information about the restoration.

One skilled in the art would understand that other labels could be substituted for alphabetic symbols of FIG. 10, and that behaviors other than the behaviors described and exemplified in FIG. 10, FIGS. 12a, 12b, and 12c, and FIGS. 14a and 14b, may be used to characterize localized behavior of the curve.

Computer executable code or programs for use in the encoding process may be provided for, example in .NET, or C++. In one embodiment, a method comprises providing computer executable instructions comprising rules or code for sampling a curve, detecting the behavior of a plurality of sets of points on the curve, associating the behavior of a set of points with a label, and linking together labels to form a chain code.

Once the characteristic curves are encoded, the chain codes may be represented as strings, and it is possible to apply well-established methods for string search and comparison. In one embodiment, Levenshtein distance is used to measure similarities between the chain code strings. This measure indicates how many edits are required to apply on one string to make it equal to another. Mathematically, the Levenshtein distance between two strings a, b is given by the following recursive formula:

$$lev_{a,b}(i, j) = \begin{cases} \max(i, j), & \text{if } \min(i, j) = 0, \\ \min \begin{cases} lev_{a,b}(i-1, j) + 1 \\ lev_{a,b(i, j-1)} + 1 \\ lev_{a,b}(i-1, j-1) + 1_{(a_i \neq b_j)}, \end{cases} & \text{otherwise.} \end{cases}$$

Where $1_{(a_i \neq b_j)}$ is the indicator function equal to 0 when $a_i = b_j$ and 1 otherwise. This metric proved to be effective in many areas, including spell checkers, search engines and DNA matching. Levenshtein distance can be used to define the similarity measure between two strings, a and b, as follows:

$$s_{a,b} = 1 - \frac{lev_{a,b}}{\max(length_a, length_b)},$$

where $lev_{a,b}$ is the Levenshtein distance between string a and b, and $length_a$ is a number of characters in string a. Similarity will be equal to 1 only when two strings are identical.

In one embodiment, a method for generating a proposal for a restoration is described that comprises searching a case repository of previously designed cases based on similarity with an encoded characteristic curve of a preparation, such as an encoded margin line, and retrieving design proposals from the database based on a similarity measurement. The method may comprise indexing the strings of the previously designed cases based on similarity measurements for efficient retrieval of design proposals. In one embodiment, the method comprises retrieving digital 3D models of the previously designed restorations that have the greatest similarity measurement as design proposals. In another embodiment, the step of retrieving design proposals comprises retrieving tooth restoration proposals that achieve a threshold similarity measurement.

A method is provided for generating a case repository of previously designed restoration cases. In one embodiment, the case repository comprises previously designed dental restoration cases (e.g., 302, 303), and information such as electronic scan data of previously designed dental restorations, 3D models, crowns (306, 307), margin line data (304, 305), preparation scans, and occlusal scans, and the like, may be generated or obtained. A database (308) may be generated that comprise metadata corresponding to the cases and associated with the 3D objects. Metadata may include margin line chain codes, strings, bounding box information, and the number of vertices. A database may comprise case specific or project information associated with specific cases.

A case repository having a vast number of previously designed restorations may be used to generate design proposals for a new tooth preparation that have high similarity measurements of characteristic curves, and corresponding digital 3D models that require less modification to be useful as a restoration design. In one embodiment, a case repository may comprise at least tens of thousands of previously designed cases per tooth number. In another embodiment, the case repository may comprise over a million previously designed restoration cases. In one embodiment, the case repository is dynamic providing instantaneous access to an updated case repository. For example, newly designed tooth restorations may be instantaneously and continuously included in the repository. Further, lower quality restoration cases may be readily removed. Illustrated in FIG. 2, a method is provided wherein, upon completion of the tooth proposal generation process, a newly designed restoration may be added to the case repository for use in subsequent restorations. In one embodiment, a newly designed restoration may be automatically added into the case repository upon completion of the restoration proposal. In other embodiments, newly designed restorations may be added if the design proposal required substantial modification prior to acceptance as a final restoration proposal. In another embodiment, the newly designed restoration may be added to the case repository where the search for restoration design proposals generated fewer than a specific number of design proposals (e.g. fewer than 10) that have a similarity measure over a threshold value (e.g. greater than 0.9), or where the retrieved proposal requires substantial modification prior to acceptance as a final restoration proposal. Newly designed restoration cases may be subject to an automated or manual quality control review process prior to inclusion of the newly designed restoration into the case repository, ensuring the quality of the cases in the case repository.

Figure 15:
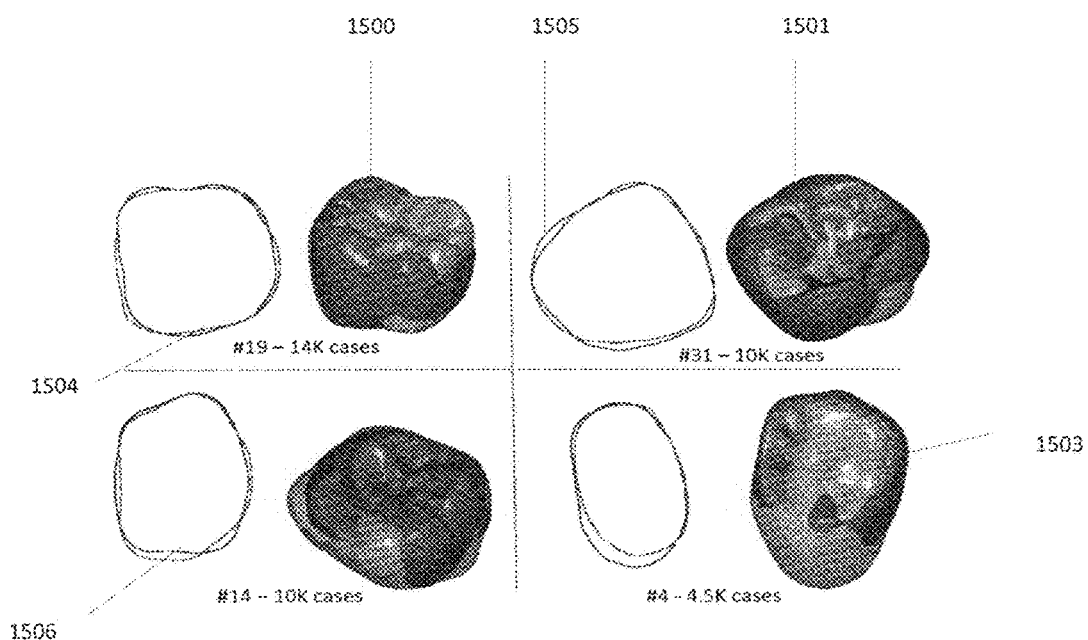
FIG. 15 shows examples of database search results by margin line similarity.

In order to test the proposed similarity measure, as depicted in FIG. 15, databases of various tooth numbers were created that comprise thousands of previously designed cases (e.g., 14,000 cases for tooth #19; 10,000 cases for tooth #31; 10,000 cases for tooth #14; and 4,500 cases for tooth #4, where the tooth numbers are based on UNI tooth number assignment). A random crown was picked for each tooth number (i.e., #19, #31, #14, and #4), and the most similar, but different, proposed case was extracted from the database when automatically generated by the curve encoding and design retrieval processes described herein. As can be seen in FIG. 15, the retrieved cases have similar margin lines (1504, 1505, 1506, and 1507) and overall shapes (1500, 1501, 1503 and 1503) when compared with the random crowns selected, as can be seen by the overlapping margin lines and similarity with overlaid 3D models of the crowns.

Figure 16:
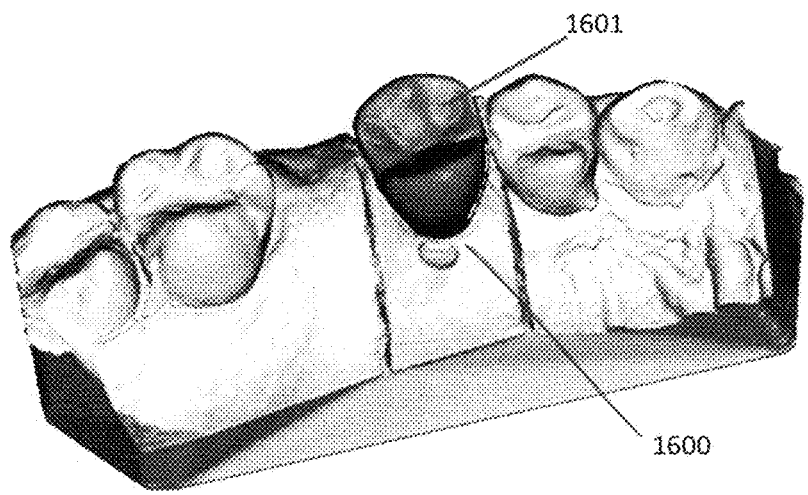
FIG. 16 shows an embodiment of an automatically generated proposal.

FIG. 16 exemplifies an automatically generated proposal (1601) for a tooth #4 (UNI), as depicted on the preparation of the tooth (1600). In this embodiment, only margin line information was utilized to generate a proposal, achieving a good fit. In a further step, additional modification of the proposal, such as crown height, may be desired, which can be accomplished, for example, by denture design software programs.

Figure 17:
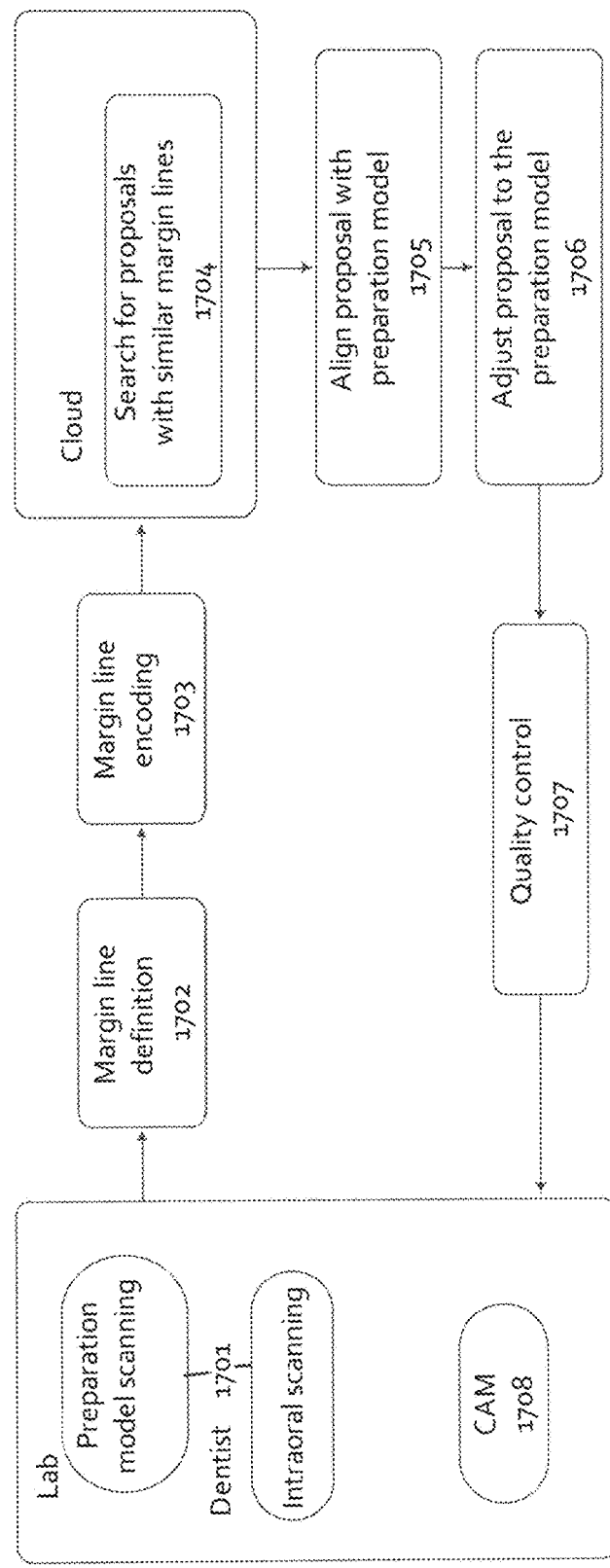
FIG. 17 shows a work flow diagram for generating restoration proposals.

In FIG. 17, a workflow diagram depicts a method of designing a dental restoration for a patient. The method comprises the steps of obtaining an electronic image file of a patient's dentition that includes a scan of at least one tooth preparation (1701) by intraoral scanning performed by the dentist, or a scan of a physical model of a preparation. The method further comprises obtaining a margin line of at least one preparation from the scan data (1702); encoding a margin line (1703); searching a case repository (FIG. 3) of previously designed restorations for design proposals that are based on similarity measurements with the margin line of the preparation (1704); optionally, indexing the previously designed restorations by similarity measurement for efficient retrieval of one proposal or a plurality of proposals; retrieving at least one design proposal that comprises a 3D image of the proposal; aligning the design proposal with the 3D image of the preparation model (1705); adjusting the design proposal to fit within the preparation model (1706); and, optionally, providing a quality control review process (1707) by assessing the suitability of the final design proposal, and thereby forming a restoration proposal. After obtaining the final restoration proposal, the method may further comprise the step of forming a physical dental restoration from the restoration proposal, such as by a computer-assisted manufacturing (CAM) process (1708) for milling restorations. It will be appreciated that alternate embodiments of the method described in FIG. 17 may be contemplated and are within the scope of this method. Moreover, processes described in the blocks do not necessarily need to be conducted in the order given, and some processes may be performed simultaneously, or optionally omitted, and additional processes may be added.

Figure 18:
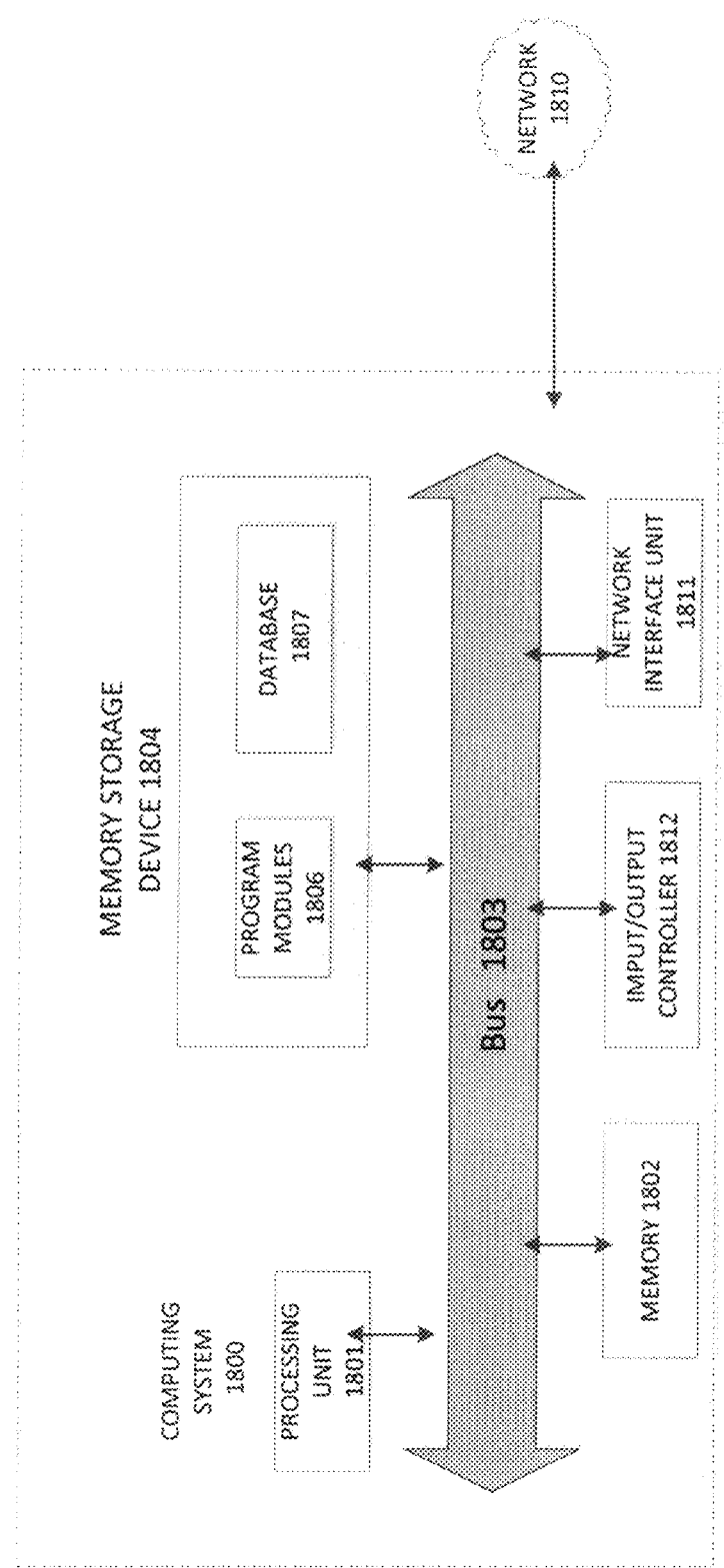
FIG. 18 shows a computing system and network connection.

FIG. 18 exemplifies a computing system that is suitable for use in performing some or all aspects of the methods according to the flow diagram of FIG. 17. A computing system (1800) may include a device such as a personal computer (309), lap top (310), handheld device (312), or work station (312), and which may include a central processing unit (CPU) (1801), a system memory (1802), and a system bus (1803) that couples the memory (1802) to the CPU (1801). The computer may also include a storage device (1804) for storing one or more programs (1806) and databases (1807). Examples of programs (1806) may include instructions for use in completing tasks described by modules represented by flow diagrams of FIG. 17 (i.e., blocks 1701-1708). The storage device (1804) and its associated computer-storage media may provide non-volatile storage for the computing system (1800).

Although the description of the computer-storage media contained herein refers to a storage device, such as a hard disk or CD-ROM, it should be appreciated by those skilled in the art that computer-storage media can be any available storage media that can be accessed by the computing system (1800). Computer-storage media may include volatile and non-volatile, removable, and non-removable media implemented in any method or technology for the non-transitory storage of information such as computer-storage instructions, data structures, program modules, or other data. For example, computer-storage media includes but is not limited to, RAM, ROM, EPROM, EEPROM, flash memory or other solid state memory technology, CD-ROM, digital versatile disks (DVD), HD-DVD, BLU-RAY, or other optical storage, magnetic cassettes, magnetic tape, magnetic disk storage devices, or any other medium which can be used to store the desired information and which can be accessed by the computing system (1800).

In one embodiment, computer-readable medium is provided having stored therein computer-executable instructions that when executed by a computing device causes the computing device to perform functions for carrying out the methods described herein. Computer-executable instructions for performing the processes described in each block of the workflow diagram of FIG. 17 may comprise a module, a segment or a portion of a program code, which includes one or more instructions executable by a processor or a computing device for implementing specific logical functions for carrying out steps in the processes described herein. The instructions may be stored on any type of computer readable medium that is suitable for the computing system used to carry out the method steps. Processes described in the flow diagram of FIG. 17 may be performed locally, using computing systems comprising programs comprising computer executable instructions, CPU's for executing instructions contained in the programs, and memory suitable for use in storing electronic files and programs as necessary for carrying out the processes described. Alternatively, one or more of the programs necessary for performing the processes contained in the flow diagram of FIG. 17 may be executed in a cloud computing system.

As indicated above, at least a portion of the methods steps described herein may occur in a cloud computing system. Cloud computing, as used herein, can refer to computing architectures in which data and programs are shared between one or more computing devices and/or server devices on a near real-time basis, thus, providing dynamic access or delivery of data and/or program modules. Cloud computing system, for purposes herein, may refer generally to a networked computer architecture in which at least a portion of the execution of programs or applications, and/or storage of data and software programs, may be provided via a computer network, in contrast to a local computing system in which both data and software are fully contained on a user's computer or computing device.

According to various embodiments, the computing system (1800) may operate in a networked environment using logical connections to remote computers through, for example the network (1810). A computing system (1800) may connect to the network (1810) through a network interface unit (1811) connected to the bus (1803). The network interface unit (1811) may connect the computing system to other networks and remote computer systems, such as CAM systems (1708) for preparing the physical restorations from a digital restoration proposal. The computing-system (1800) may also include an input/output controller (1812) for receiving and processing input from a number of input devices (not shown) including a keyboard, a mouse, a microphone and a game controller. Similarly, the input/output controller (1812) may provide output to a display or other type of output device. The bus (1803) may enable the CPU (1801) to read code and/or data to/from the storage device (1804) or other computer-storage media.

The program modules (1806) may include software instructions that, when loaded into the CPU (1801) and executed, cause the computing system (1800) to perform at least some of the steps of the work flow diagram of FIG. 17, in a cloud computing system. The program modules (1806) may also provide tools or techniques by which the computing-system (1800) may participate within the overall systems or operating environments. In one embodiment, program modules (1806) may implement interfaces for providing communication between local computing systems of a dentist or a dental laboratory (FIG. 3 at 309-312) and services or processes that operate in a cloud computing system.

Processes performed in a cloud-based computing system may be used herein to refer to a process, processes or a portion of a process, that is conducted over a network (1810) (for example, Internet) by dentists or dental laboratories. Cloud computing systems enable multiple users to have access to computing resources such as networks, servers, storage and databases, applications and services. Multiple computing systems may simultaneously connect to a cloud computing system, and have access to the same computing resources, such as computing power, storage, data, and applications comprising instructions for performing the processes of the flow diagram of FIG. 17. For example, multiple users may simultaneously access and search a case repository of previously designed restorations (301) and an associated database (308) located within a cloud computing system (300), or design program modules for modifying retrieved proposals. In one embodiment, the cloud computing system comprises an elastic computing system where resources, such as computing power, may be automatically added or decreased based on, for example, the number of simultaneous connections by computing devices for accessing the resources and processes disclosed herein.

In one embodiment, patient files may be stored on a remote server rather than locally on a storage medium. Cloud computing applications may store copies of data and/or executable programs at remote server devices, allowing users such as dentists or dental laboratories to download or access at least some of this data and program logic as needed for performing at least a portion of the processes described herein by way of personal computers, tablets, handheld devices, and computer-operated machinery and devices.

In one embodiment, the cloud computing system may include a number of computing systems and devices coupled to or configured to be capable of communicating with components of the cloud. For example, a computing system (1800), a host system, a scanning system, and a CAM system may all be coupled to the cloud computing system. The host may be any type of computing device or transmitter that is configured to transmit data to the cloud such as a computer, a laptop computer, a mobile device and the like. Communication links between computing devices and cloud computing systems may include wired connections, such as a serial or parallel bus, or wireless links, such as Bluetooth, IEEE 802.11 (including amendments thereto), and the like. The system may further include access points by which computing devices may communicate with the cloud, such as through wireless access points or a wireless router, a base station in a cellular network that provides internet connectivity, and the like.

In one embodiment, a method for generating a design proposal for a tooth restoration is provided that comprises the computer-implemented steps of:
  a. obtaining data for a tooth preparation that comprises a chain code for an encoded margin line of a tooth preparation;
  b. accessing a case repository of previously designed dental restoration cases, wherein each case comprises a chain code for an encoded margin line and a digital 3D model of a restoration;
  c. searching the case repository by measuring similarity between the chain code of the tooth preparation and the chain codes of the previously designed dental restorations, and indexing at least a portion of the previously designed dental restorations by similarity measurements;
  d. retrieving a plurality of digital 3D models of the previously designed dental restorations as design proposals for the tooth preparation based on the similarity measurements of the chain codes; and
  e. selecting one design proposal as a tooth restoration proposal.

In one embodiment, the method further comprises the step of lining a margin of the tooth preparation to form the margin line which may be performed in a cloud computing system. In another embodiment, the method further comprises encoding the margin line of the tooth preparation, and the step of encoding the margin line may be performed in a cloud computing system. In a further embodiment, the case repository may be stored in a cloud computing system. In a still further embodiment, searching the case repository may be performed in a cloud computing system. In another embodiment, performing similarity measurements may be performed in a cloud computing system. In a further embodiment, selecting one of the proposals may be performed in a cloud computing system. In still another embodiment, modifying the design proposal to fit the preparation may be performed in a cloud computing system. In one embodiment, all or some of the process steps may be performed in a cloud computing system.

A system for obtaining a design proposal is also provided that comprises one or more computing devices, at least one of which is configured to operate in a cloud computing system, and a plurality of program modules having instructions that are executable by the one or more computing devices, that provide instructions for performing process steps to obtain a design proposal. Program modules suitable for use in this system comprise one or more of: a) obtaining a digital 3D model of a dental preparation comprising a shape descriptor, and digital data comprising a representation of the shape descriptor of the dental preparation; b) accessing a case repository stored in the cloud computing system comprising a plurality of previously completed dental restoration cases wherein each case comprises i) a 3D digital model of the completed dental restoration comprising a shape descriptor, and i) digital data that comprises a representation of the shape descriptor of the previously completed dental restoration; c) searching the digital data by similarity between the shape descriptor of the dental preparation and the shape descriptors of the previously completed restoration cases; d) retrieving a plurality of 3D digital models of the previously completed restoration cases that have shape descriptors most similar to the shape descriptors of the dental preparation as design proposals; and e) selecting one proposal as a restoration proposal.

In one embodiment, the system comprises a first computing device is configured to operate in a cloud computing system, and a second computing device is connected to the first computing device through an internet connection. In another embodiment, the second computing device comprises a display module for viewing the restoration proposal, and optionally, a plurality of the process steps may be performed in a cloud computing system via program modules that are stored or run at a location that is remote from the second computing device. In a further embodiment, the second computing device comprises a CPU, a memory, and at least one program module to perform at least one of the process steps for obtaining a design proposal, wherein a plurality of the program modules may be run on the second computing device, and only one or a few process steps are performed in the cloud. In another embodiment, the second computing device comprises at least one program module having executable instructions for retrieving the 3D digital models that correspond to the design proposals, selecting one design proposal, and optionally, modifying the design proposal to form a restoration proposal, and the processes are performed on the second computing device.

In addition to dental applications, the presently disclosed methods may have applications in areas other than dentistry. Efficient shape encoding and search may be utilized in systems such as 3D search engines (e.g., Google 3D Warehouse), real-time tracking systems (e.g., Microsoft Kinect) and others. It should be understood that arrangements described herein are for purposes of example only. As such, those skilled in the art will appreciate that other arrangements and other elements such as machines, interfaces, functions, orders, and groupings of functions, and the like, can be used. Further, elements described as functional elements may be implemented as discrete components or in combination with other components. Various alternatives, modifications, variations, or improvements therein may be subsequently made by those skilled in the art which fall within the scope and spirit of the principles of the present disclosure.

We claim:

1. A method for generating a design proposal for a dental restoration for a patient comprising:
   performing a plurality of functions associated with the design proposal using a computing system, the functions comprising:
   a. obtaining data for a tooth preparation of the patient to be restored by a dental restoration, wherein the data for the tooth preparation comprises a chain code for an encoded margin line of the tooth preparation;
   b. accessing a case repository stored in the computing system's storage device and comprising a plurality of cases of previously designed dental restorations, wherein each case of previously designed dental restorations comprises: i) a chain code for an encoded margin line of a previously designed dental restoration and ii) a digital 3D model of a dental restoration;
   c. obtaining a plurality of similarity measurements by measuring similarity between the chain code for the encoded margin line of the tooth preparation of the patient and the chain code for the encoded margin line of the previously designed dental restoration of each case,
   d. indexing at least a portion of the previously designed dental restorations by the similarity measurements and retrieving a plurality of digital 3D models of the previously designed dental restorations based on the similarity measurements;
   e. selecting one of the digital 3D models retrieved from step d) as a dental restoration proposal for the patient; and
   f. generating a dental restoration design for the tooth preparation of the patient from the dental restoration proposal; and
   forming a physical dental restoration from the dental restoration design using a computer aided manufacturing (CAM) system.

2. The method of claim 1, further comprising the step of lining a margin of the tooth preparation to form the margin line, and the step of lining the margin is performed in a cloud computing system.

3. The method of claim 1, further comprising the step of encoding the margin line of the tooth preparation, and the step of encoding the margin line is performed in a cloud computing system.

4. The method of claim 1, wherein the case repository is stored in a cloud computing system.

5. The method of claim 1, wherein the step of measuring similarity is performed in a cloud computing system.

6. The method of claim 1, further comprising the step of displaying the tooth preparation on a display monitor as a 3D image.

7. The method of claim 1, further comprising the step of modifying, using the computing system, the dental restoration proposal to fit the tooth preparation.

8. The method of claim 1, wherein the method further comprises aligning, on the computing system's display device, the dental restoration proposal and a 3D image of the tooth preparation to generate the dental restoration design.

9. The method of claim 8, wherein the step of aligning comprises displaying an image of the dental restoration proposal and an image of the tooth preparation on a display monitor.

10. The method of claim 1, wherein the chain codes for an encoded margin lines of the tooth preparation and the previously designed dental restorations are saved and searched as strings using the computing system.

11. A method for designing a dental restoration for a tooth to be restored for a patient comprising:
performing a plurality of functions associated with the dental restoration design using a computing system, the functions comprising:
a. encoding a margin line of a tooth preparation of the patient comprising
i. obtaining a digital 3D model of the tooth preparation to be restored wherein the tooth preparation comprises a margin;
ii. virtually marking the margin of the tooth preparation to form the margin line;
iii. encoding the margin line by a curve encoding process comprising:
sampling the margin line at sample points;
identifying local behavior over a set of adjacent sample points; and
assigning a label to a sample point that identifies the behavior; and
iv. linking the labels together to form a chain code;
b. accessing a case repository stored in the computing system's storage device and comprising a plurality of cases of previously designed dental restorations wherein each case comprises i) digital 3D model of a previously designed dental restoration and ii) a chain code for an encoded margin line of the previously designed dental restoration;
c. obtaining a plurality of similarity measurements by obtaining a measure of similarity between the chain code of the previously designed dental restoration and the chain code of the tooth preparation of the patient, for the plurality of cases;
d. retrieving a plurality of digital 3D models of the plurality of cases of previously designed dental restorations based on the plurality of similarity measurements;
e. selecting one of the digital 3D models as an initial design for the dental restoration for the patient; and
f. modifying the selected digital 3D model to fit the tooth preparation to form generate a dental restoration design for the tooth preparation; and
forming a physical dental restoration from the dental restoration design using a computer aided manufacturing (CAM) system.

12. A method for generating a dental restoration design for a tooth of a patient in need of restoration comprising:
performing a plurality of functions associated with the dental restoration design using a computing system, the functions comprising:
a) obtaining i) a digital 3D model of a tooth preparation of the patient comprising a shape descriptor, and ii) digital data that represents the shape descriptor of the tooth preparation of the patient;
b) accessing a case repository stored in the computing system's storage device and comprising a plurality of previously designed dental restoration cases wherein each case comprises
i) a digital 3D model of a previously designed dental restoration comprising a shape descriptor, and
ii) digital data that represents the shape descriptor of the previously designed dental restoration;
c) measuring similarity between the shape descriptor of the tooth preparation of the patient and the shape descriptor of the previously designed dental restoration for the plurality of previously designed dental restoration cases to obtain a plurality of similarity measurements;
d) selecting more than one of the plurality of previously designed dental restoration cases based on the plurality of similarity measurements;
e) retrieving, from the computing system's storage device, a plurality of digital 3D models corresponding to the selected previously designed dental restoration cases from step d); and
f) generating a dental restoration design for the tooth preparation from one of the plurality of digital 3D models retrieved in step e); and
forming a physical dental restoration from the dental restoration design using a computer aided manufacturing (CAM) system.

13. The method of claim 12, further comprising displaying, on the computing system's display device, at least one of the plurality of digital 3D models from step e) and selecting one as a dental restoration proposal.

14. The method of claim 13, further comprising modifying the selected restoration proposal to generate the dental restoration design.

15. A system for obtaining a dental restoration proposal to restore a tooth of a patient comprising:
one or more computing devices, at least one of which is configured to operate in a cloud computing system, and a plurality of program modules having instructions, wherein at least one program module is stored on a non-transitory computer-readable medium, that are executable by the one or more computing devices, that provide instructions for performing process steps to obtain a dental restoration proposal comprising:
a) obtaining i) a digital 3D model of a tooth preparation of the tooth of the patient to be restored comprising a shape descriptor, and ii) digital data comprising a representation of the shape descriptor of the tooth preparation;
b) accessing a case repository stored in the cloud computing system comprising a plurality of cases of previously designed dental restorations wherein each case comprises
i) a 3D digital model of a previously designed dental restoration comprising a shape descriptor, and
ii) digital data that comprises a representation of the shape descriptor of the previously designed dental restoration;
c) generating similarity measurements by measuring the similarity between i) the digital data that comprises the representation of the shape descriptor of the tooth preparation of the patient and ii) the digital data that comprises the representation of the shape descriptor of the previously designed dental restoration, for the plurality of cases;
d) retrieving a plurality of 3D digital models of the plurality of cases of previously designed dental restorations from the case repository based on the similarity measurements of the shape descriptors;

e) generating a dental restoration design for the tooth preparation of the patient that corresponds to one of the plurality of 3D digital models retrieved from the case repository; and f) forming a physical dental restoration from the dental restoration design using a computer aided manufacturing (CAM) system.

16. The system of claim 15, wherein a first computing device is configured to operate in a cloud computing system, and a second computing device is connected to the first computing device through an internet connection.

17. The system of claim 16, wherein the computing system comprises a display module for viewing an image of the digital model of the tooth preparation.

18. The system of claim 16, wherein the second computing device comprises a CPU, a memory, and at least one program module to perform at least one of the process steps for obtaining a dental restoration proposal.

19. The system of claim 15, wherein the system comprises a display module for viewing an image of the dental restoration proposal.

20. The system of claim 19, wherein the second computing device comprises at least one program module having executable instructions for retrieving the plurality of 3D digital models, generating the dental restoration design, and optionally, modifying the dental restoration design to fit the tooth preparation of the patient.

* * * * *